US00PP26899P3

(12) United States Plant Patent
Draper et al.

(10) Patent No.: US PP26,899 P3
(45) Date of Patent: Jul. 5, 2016

(54) BLUEBERRY PLANT NAMED 'PINNACLE'

(50) Latin Name: *Vaccinium corymbosum* Linnaeus
Varietal Denomination: Pinnacle

(71) Applicant: North Carolina State University, Raleigh, NC (US)

(72) Inventors: Arlen D. Draper, Payson, AZ (US); James Ralph Ballington, Cary, NC (US); Charles Michael Mainland, Wilmington, NC (US); William Terry Bland, Wilmington, NC (US)

(73) Assignees: NORTH CAROLINA STATE UNIVERSITY, Raleigh, NC (US); THE UNITED STATES OF AMERICA, AS REPRESENTED BY THE SECRETARY OF AGRICULTURE, Washington, DC (US)

( * ) Notice: Subject to any disclaimer, the term of this patent is extended or adjusted under 35 U.S.C. 154(b) by 105 days.

(21) Appl. No.: 14/120,395

(22) Filed: May 16, 2014

(65) Prior Publication Data

US 2015/0334890 P1 Nov. 19, 2015

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — June Hwu
(74) *Attorney, Agent, or Firm* — Myers Bigel & Sibley, P.A.

(57) ABSTRACT

'Pinnacle' is a new and distinct variety of blueberry plant that has the following unique combination of desirable features outstanding in a new variety. 'Pinnacle' provides season ripening when prices remain high and consistently good yields of large size fruit. In addition, 'Pinnacle' provides high percentages of fruit in very large diameter categories, which are tailored for premium market outlets, very good fruit color and quality, excellent fruit firmness and fruit with very good post-harvest shelf-life.

6 Drawing Sheets

Latin name of the genus and species: The Latin name of the novel blueberry cultivar disclosed herein is *Vaccinium corymbosum* Linnaeus.

Variety denomination: The inventive cultivar of *Vaccinium corymbosum* disclosed herein has been given the varietal denomination 'Pinnacle'.

BACKGROUND OF THE INVENTION

The present invention relates to a new and distinct cultivar of *Vaccinium corymbosum* Linnaeus (blueberry) grown as a fruiting woody shrub for commercial agriculture. Blueberries are typically consumed both fresh and in a number of processed products. The new and distinct variety of blueberry (*Vaccinium corymbosum* Linnaeus) originated from the hand pollinated cross of NC 1408 (unpatented) (female parent)× 'Bluechip' (unpatented) (male parent) made in a greenhouse at Beltsville, Md. and was assigned experimental selection number US 508 at that time. US 508 has since then been renamed 'Pinnacle'.

'Pinnacle' differs from its female parent NC 1408 in plant habit and fruit size. Whereas NC 1408 has a narrowly erect plant habit with few main stems, 'Pinnacle' has a semi-erect plant habit with numerous main stems. Fruit size for NC 1408 is medium, while fruit size of 'Pinnacle' is large. 'Pinnacle' differs from 'Bluechip' in plant habit and ripening season. Whereas 'Bluechip' has an erect plant habit, the plant habit of 'Pinnacle' is semi-erect and 'Bluechip' is midseason ripening, while Pinnacle is early ripening.

'Pinnacle' was selected for its superior earliness, size, color, and quality in 1987 from a soil adaptation pot culture experiment established at Beltsville, Md. Plants of 'Pinnacle' were grown in replicate observation trials in 1991 and in 1992 at the North Carolina State University Horticultural Crops Research Station at Castle Hayne, N.C.

Based on its performance in the replicated trial at Castle Hayne, N.C., 'Pinnacle' was propagated by hardwood cuttings and established in two additional replicated trials. One was a commercial blueberry grower at Rowan, N.C., under a Memorandum of Agreement with North Carolina State University, whereby the grower provided the land and care of the plants, and the University retained ownership of the plants. The other additional replicated trial was established at the Horticultural Crops Research Station at Castle Hayne, N.C. Plants of Pinnacle were also established in grower observation adaptation trials across the commercial blueberry region in eastern North Carolina in 2010 and 2011 under Memoranda of Agreements with North Carolina State University whereby the growers provided the land and care of the plants, and the University retained ownership of the plants. Plants of this new variety have remained true to type through successive cycles of asexual propagation. This new variety has been named the 'Pinnacle' cultivar.

SUMMARY OF THE INVENTION

The following are the unique and distinguishing characteristics of this new cultivar when grown under standard horticultural practices at North Carolina State University Horticultural Crops Research Station, Castle Hayne, N.C.

'Pinnacle' is a new and distinct cultivar of blueberry plant with the following combination of desirable characteristics outstanding in a new variety.

1. Early season ripening when prices remain high.
2. Consistently good yields of large size fruit.
3. High percentages of fruit in very large diameter categories which are tailored for premium market outlets.
4. Very good fruit color and quality and excellent fruit firmness.
5. Fruit with very good post-harvest shelf-life.

'Pinnacle' is highly successful with propagation by hardwood or softwood cuttings and has remained true to type across generations of asexual propagation in Beltsville, Md. The 'Pinnacle' plant is moderately vigorous and performs best on a good "highbush blueberry soil" such as a Berryland. The chilling requirement for dormant buds is 600-700 hours below 45° F. The plants of 'Pinnacle' are semi-upright in habit, and the flowers are self: fertile and produce abundant pollen.

BRIEF DESCRIPTION OF THE DRAWINGS

This new blueberry is illustrated by the accompanying photographs, which show the plant's form, foliage and inflorescences. The photographs in the drawings were made using digital photography techniques and illustrate colors as true as can be reasonably obtained when using these techniques. Colors in the photographs may differ slightly from the color values cited in the detailed botanical description, which accurately describe the colors of the new *Vaccinium corymbosum* variety. All photographs were taken from plants growing at the Horticultural Crops Research Station at Castle Hayne, N.C.

DETAILED BOTANICAL DESCRIPTION

Figure 1:
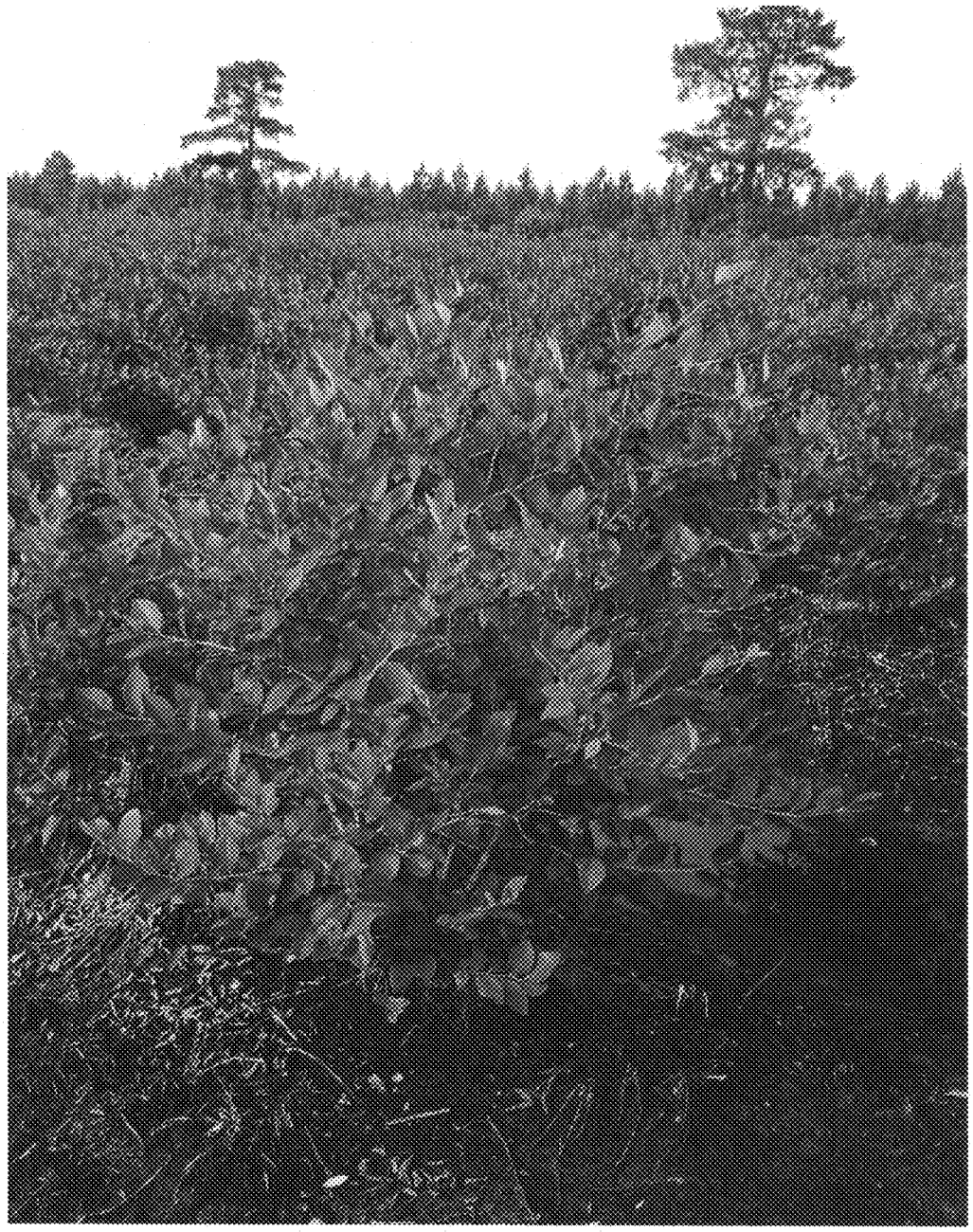
FIG. 1 is a color photograph taken in August 2013 illustrating the typical plant habit of 'Pinnacle' at three years of age.
Figure 2:
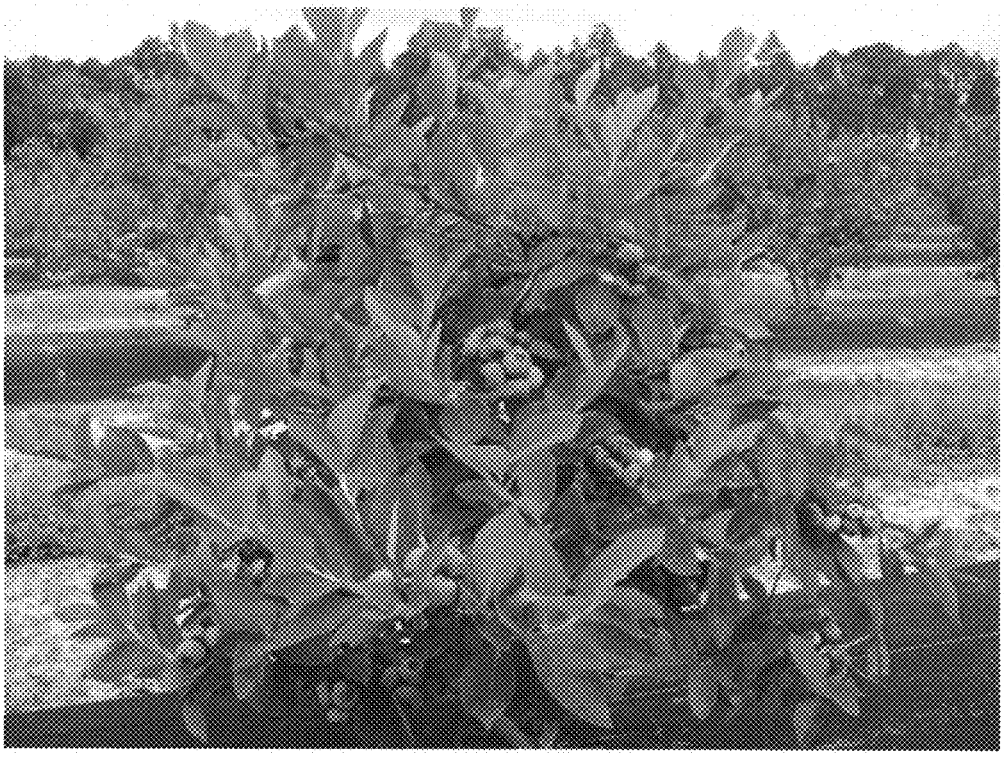
FIG. 2 is a color photograph taken in June 2013 illustrating the typical fruit of 'Pinnacle' still on a three year old bush.

The following is a detailed description of the botanical characteristics of the new and distinct variety of *Vaccinium corymbosum* Linnaeus plant known by the denomination 'Pinnacle'. The observations below are from mature plants grown in a replicated trial at a standard commercial plant spacing of 3' between plants in rows and 10' between rows, at Castle Hayne, N.C. (FIGS. 1 and 2). Those skilled in the art of cultivar description and evaluation will appreciate that certain characteristics of a variety will vary with older or, conversely, younger plants. 'Pinnacle' has not been observed under all possible environmental conditions. Where dimensions, sizes, colors and other characteristics are given, it is to be understood that such characterizations are approximations or averages set forth as accurately as practicable. The phenotype of the variety may differ from the description herein with variations in the environment such as season, temperature, light intensity, day length and cultural conditions. Color notations are based on The Royal Horticultural Society Colour chart, The Royal Horticultural Society, London, UK, 4th edition, 2001.

For purposes of a botanical description, 'Pinnacle' was compared to 'New Hanover' (U.S. Plant Pat. No. 19,990), a recent release from North Carolina State University, and 'O'Neal' (unpatented), the very early ripening standard commercial blueberry cultivar in North Carolina. The female parent of 'Pinnacle', NC 1408, is no longer extant, therefore it was not possible to use NC 1408 to make direct measureable comparisons with 'Pinnacle' for the purpose of this application. The male parent of 'Pinnacle', 'Bluechip' is extremely susceptible to the stem blight fungus (*Botryosphaeria dothidea*) to the point that it is impractical to establish and maintain plants for comparison purposes; therefore it was not possible to use 'Blue Chip' to make direct measureable comparisons with 'Pinnacle' as well. The data in the tables is an average of data collected from 2005-2009 at Castle Hayne and Rowan, N.C. The remaining botanical descriptive data was collected from four year old plants at Castle Hayne, N.C.

TECHNICAL DESCRIPTION OF THE VARIETY

Plant:

*Dimensions*.—Pinnacle — 1.3 m height, 1.0 m diameter, H/D ratio 1.30. New Hanover — 1.6 m height, 1.4 m diameter, H/D ratio 1.14. O'Neal — 1.5 m height, 1.0 diameter, H/D ratio 1.50.

*Growth habit*.—Semi-upright for Pinnacle, New Hanover and O'Neal.

*Mature stem diameter*.—Pinnacle — 2.5 cm. New Hanover — 3.2 cm. O'Neal — 2.5 cm.

*Mature stem length*.—Pinnacle — 0.7 m. New Hanover — 1.0 m. O'Neal — 1.2 m.

*Number of renewal stems*.—Pinnacle — 0.5. New Hanover — 1.0. O'Neal — 1.5.

*Internode length on first flush growth*.—Pinnacle — 14.0 cm. New Hanover — 12.0 cm. O'Neal — 14.0 cm.

*Dormant mature stem color*.—Gray-brown (RHS 199D) for Pinnacle, New Hanover and O'Neal.

*Dormant one year stem color*.—Pinnacle — grayed-red (RHS 180A) on exposed surface, yellow-green (RHS 144A) on unexposed surface. New Hanover — red (RHS 46A) on exposed and unexposed surfaces. O'Neal — red (RHS 46A) on exposed surface, grayed-orange (RHS 167C) on unexposed surface.

*First flush growth stem color*.—Pinnacle — grayed-orange (RHS 172A) on exposed surface, yellow-green (RHS N144B) on unexposed surface. New Hanover — grayed-red (RHS 181A) on exposed surface, yellow-green (RHS N144C) on unexposed surface. O'Neal — grayed-red (RHS 181B) on exposed surface, yellow-green (RHS N144A) on unexposed surface.

*First vegetative bud burst*.—Pinnacle — medium.

*Pubescence on summer and one year dormant stems*.—Pinnacle — none (glabrous). New Hanover — very fine, moderately dense. O'Neal — fine, moderately dense.

Leaves:

*Leaf blade dimensions*.—Pinnacle — 55 mm length, 27 mm width, L/W ratio 2.04. New Hanover — 52 mm length, 28 mm width, L/W ratio 1.86. O'Neal — 51 mm length, 26 mm width, L/W ratio 1.96.

*Leaf petiole length*.—Pinnacle — 3.8 mm. New Hanover — 3.4 mm. O'Neal — 3.8 mm.

*Leaf shape*.—Pinnacle — narrowly elliptic (to occasionally elliptic obovate). New Hanover — elliptic to narrowly elliptic (to occasionally elliptic obovate). O'Neal — elliptic.

*Leaf apex angle*.—Pinnacle — acuminate to occasionally acute. New Hanover — acute to occasionally acuminate. O'Neal — acuminate.

*Leaf base angle*.—Acute on Pinnacle, New Hanover, and O'Neal.

*Leaf margin*.—Pinnacle and New Hanover — entire to occasionally serrulate on the basal half. O'Neal — entire.

*Leaf pubescence*.—None for Pinnacle, New Hanover or O'Neal.

*Leaf glands*.—None on either surface for Pinnacle, New Hanover or O'Neal.

*Leaf color*.—Pinnacle .— green (RHS 137A) on the adaxial surface, yellow-green (RHS 148B) on the abaxial surface. New Hanover and O'Neal — green (RHS 137B) on the adaxial surface, yellow-green (RHS 147C) on the abaxial surface.

Flowers:

*Number of flower petals*.—Five for Pinnacle, New Hanover and O'Neal, fused completely along the margins into a corolla tube so that they cannot be separated for individual measurements. Slight but not prominent ridges are present on the corolla tube.

*Number of flowers per inflorescence*.—Pinnacle — 6. New Hanover — 8. O'Neal — 7.

*Flower dimensions*.—Pinnacle — 8.5 mm length, 5.0 mm width, L/W ratio 1.70. New Hanover — 9.5 mm length, 7.7 mm width, L/W ratio 1.23. O'Neal — 10.0 mm length, 6.5 mm width, L/W ratio 1.54.

*Length of the single style*.—Pinnacle — 7 mm. New Hanover — 8 mm. O'Neal —8 mm.

*Length of stamens*.—Pinnacle — 5.0 mm. New Hanover — 5.7 mm. O'Neal — 6.7 mm.

*Flower shape*.—Pinnacle — cylindrical. New Hanover — cylindrical to cylindro-urceolate. O'Neal — cylindro-urceolate.

*Color of petals on fully opened flowers*.—White (RHS 155B-155C) for Pinnacle, New Hanover and O'Neal.

*Calyx*.—Pinnacle: calyx basin is shallow to medium in depth.

Figure 3:
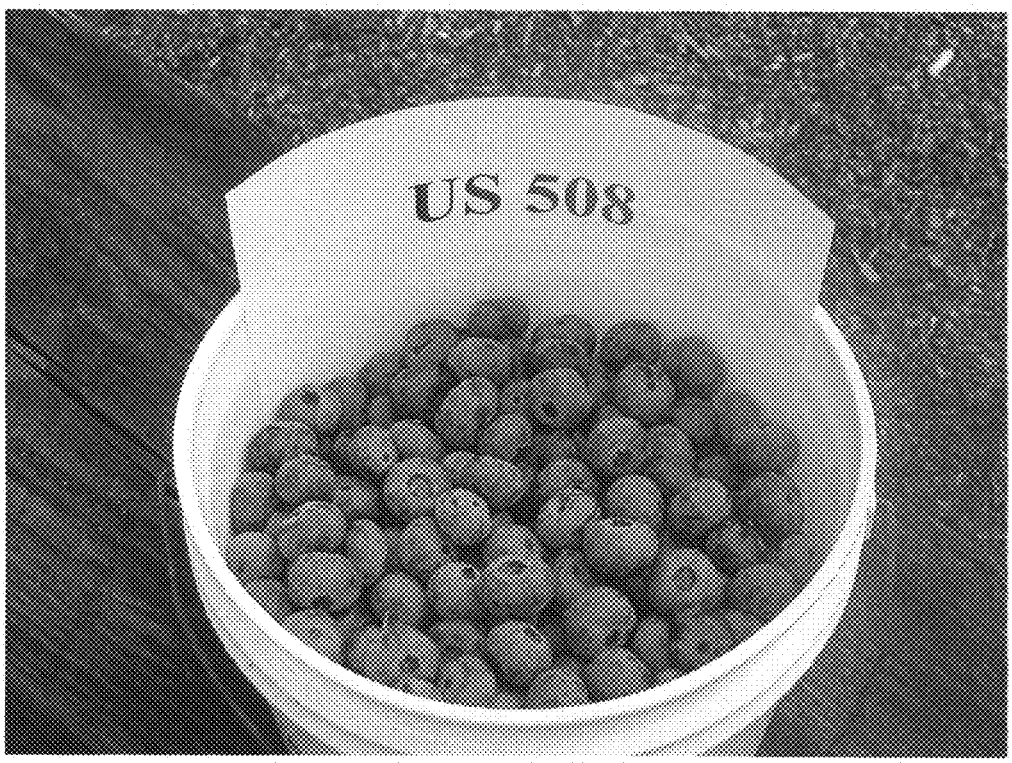
FIG. 3 is a color photograph taken in June 2010 providing a closer view of the typical fruit of 'Pinnacle' from six year old plants.

Fruit: (see, FIGS. 2 and 3).

*Fruit dimensions*.—Pinnacle — 13 mm length, 20 mm diameter, L/D ratio 0.65. New Hanover — 12 mm length, 19 mm diameter, L/D ratio 0.63. O'Neal — 13 mm length, 18 mm diameter, L/D ratio 0.72.

*Fruit shape*.—Oblate for Pinnacle, New Hanover and O'Neal.

*Fruit pedicel length*.—Pinnacle — 4-5(6) mm. New Hanover — 4-5(6) mm. O'Neal — 4-6 mm.

*Fruit pedicel color*.—Pinnacle — upper and lower surfaces yellow-green (RHS 144A). New Hanover — upper surface red (RHS 46B), lower surface yellow-green (RHS 145B). O'Neal — upper surface red (RHS 45A), lower surface yellow-green (RHS 145B).

*Fruit picking scar diameter*.—Pinnacle — 1.7 mm. New Hanover — 3.0 mm. O'Neal — 1.0 mm.

*Fruit calyx orientation and prominence*.—Pinnacle — Varies from appressed against the apex to upright; not prominent. New Hanover — Varies from appressed to one or more lobes upright; not prominent. O'Neal — Varies from appressed to upright; not prominent.

*Fruit calyx diameter*.—5-7 mm for Pinnacle, New Hanover and O'Neal.

*Fruit color with bloom* (*epicuticular wax*).—Pinnacle and New Hanover — violet-blue (RHS 97C). O'Neal — violet-blue (RHS 97B).

*Fruit color without bloom*.—Black (RHS 202A) for Pinnacle, New Hanover and O'Neal.

*Fruit cluster density*.—Pinnacle — medium.

*Fruit acidity*.—Pinnacle — high.

*Fruiting type*.—Pinnacle — produces fruit on one-year shoots only.

Fruit sepals:

*Fruit sepal number*.—Five for Pinnacle, New Hanover and O'Neal.

*Fruit sepal shape*.—Ovate for Pinnacle, New Hanover and O'Neal.

*Fruit sepal length*.—Pinnacle — 1.0-2.0 mm. New Hanover — 1.5-2.0 mm. O'Neal — 1.5-2.0 mm.

*Fruit sepal width*.—Pinnacle — 3-4 mm. New Hanover — 3-4 mm. O'Neal — 3 mm.

*Fruit sepal apex*.—Pinnacle — acuminate. New Hanover — acute. O'Neal — acute to occasionally acuminate.

*Fruit sepal base*.—Fused to the fruit skin on Pinnacle, New Hanover and O'Neal.

*Fruit sepal margin*.—Entire for Pinnacle, New Hanover and O'Neal.

*Fruit sepal outer surface color*.—Pinnacle and New Hanover — violet-blue (RHS 97C). O'Neal — violet-blue (RHS 97B).

*Fruit sepal inner surface color*.—Black (RHS 202A) for Pinnacle, New Hanover and O'Neal.

*Fruit sepal attitude*.—Pinnacle: variable, from flat to erect.

Seeds:

*Number of fully developed seeds per berry*.—Pinnacle — 37. New Hanover — 35. O'Neal — 39.

*Seed dimensions*.—Pinnacle — 1.7 mm length, 1.0 mm width, L/W ratio 1.7. New Hanover — 2.0 mm length, 1.0 mm width, L/W ratio 2.0. O'Neal — 1.8 mm length, 1.0 mm width, L/W ratio 1.8.

*Seed shape*.—Principally depressed-ovate for Pinnacle, New Hanover and O'Neal.

For technical (pomological) description purposes 'Pinnacle' was also compared to 'New Hanover' and 'O'Neal' (Tables 2-8), except for bloom dates where 'Star' (relatively new early standard) and 'Croatan' (old North Carolina standard) were also included to provide a broader picture for this trait (Table 1). Data from either the replicated trial from Rowan, N.C., or Castle Hayne, N.C., were randomly chosen to be included in the tables, except for yield per plant (Table 3) (where data from Rowan was more representative due to ongoing spring frost problems at Castle Hayne), and fruit color (Table 5) and fruit firmness (Table 6) (where data from Castle Hayne were determined to be more representative due to less handling and transport of the fruit). Unless otherwise indicated, these were four replications that included four plants per rep.

Time of Flowering:

Table 1 presents representative bloom data comparing 'Pinnacle' to four other blueberry cultivars, 'Star', 'New Hanover', 'O'Neal', and 'Croatan'. 'Pinnacle' was 25 days later than 'O'Neal' and 'New Hanover', 11 days later than than 'Star', and 25 days earlier than 'Croatan' for date of first bloom. 'Pinnacle' was 20 days later than 'Star', 5 days later than 'O'Neal' and 'New Hanover', and 12 days earlier than 'Croatan' for date of 25 percent bloom. However it reached full bloom on the same date as 'O'Neal' and 'New Hanover'. This means that after reaching 25% bloom, bloom accelerates very rapidly for 'Pinnacle'.

TABLE 1

Time of flowering of blueberry cultivars, Castle Hayne, NC. 2006[1]

| | Bloom dates | | |
|---|---|---|---|
| Cultivar | First bloom | 25% bloom | Full bloom |
| Star | Feb. 17 | Mar. 8 | Mar. 28 |
| New Hanover | Feb. 6 | Mar. 23 | Apr. 4 |
| O'Neal | Feb. 6 | Mar. 23 | Apr. 4 |
| Pinnacle | Mar. 3 | Mar. 28 | Apr. 4 |
| Croatan | Mar. 28 | Apr. 9 | Apr. 14 |

[1]Estimated from field observations.

Pollination Requirements:

The flowers of 'Pinnacle' are self-fertile.

Pollen Production:

'Pinnacle' flowers produce abundant pollen.

Season of Ripening:

Season of ripening is represented by percent ripe fruit by early June (Table 2). On average, 'Pinnacle' was 2-3 days later than 'O'Neal' and 3-7 days earlier than 'New Hanover'. Since 'O'Neal' is considered very early ripening, this places 'Pinnacle' in the early ripening season. This is significant because a high percent of total production of 'Pinnacle', as well as 'O'Neal' and 'New Hanover', falls within the mid-May through early June North Carolina market window when no other major blueberry production region is shipping fruit to North Carolina markets.

TABLE 2

Season of ripening for blueberry cultivars across locations. 2005-2007

| | Percent ripe by early June | |
|---|---|---|
| Cultivar | Rowan[1] | Castle Hayne[2] |
| New Hanover | 66 | 77 |
| O'Neal | 71 | 86 |
| Pinnacle | 69 | 84 |

[1]Average for 2005 and 2007, Jun. 4-Jun. 6.
[2]Average for 2005-2007,Jun. 6-Jun. 8.

Yield Per Plant:

The yield of 'Pinnacle' was equal to 'New Hanover' and superior to 'O'Neal' in 2005 (Table 3). In 2007, yield of 'Pinnacle' was equal to 'O'Neal', but not to 'New Hanover'. However, there were no significant differences among the three cultivars for average yield across the two years as indicated by the abbreviation "n.s."." (i.e., not significant), after the values in column 4, below.

TABLE 3

Total yield of blueberry cultivars at Rowan, NC. 2005 and 2007.[1]

| | Yield (grams/plant)[2] | | |
|---|---|---|---|
| Cultivar | 2005 | 2007 | Average |
| New Hanover | 2578a | 4179a | 3378 n.s. |
| O'Neal | 1462b | 2676b | 2069 n.s. |
| Pinnacle | 2531a | 2738b | 2635 n.s. |

[1]2006 not included because commercial pickers harvested fruit prior to our harvest one week midway through the season.
[2]Numbers not followed by the same letter are significantly different (LSD 0.05);
n.s. = not significant.

Fruit Size Characteristics:

Average berry weight of 'Pinnacle' was significantly greater than 'O'Neal', but not significantly greater than 'New Hanover' berries (Table 4). 'Pinnacle' also had a much higher percent fruit in the larger diameter catagories (% greater than 16 mm and 18 mm diameter) than either 'New Hanover' or 'O'Neal'. The latter trait is significant today because some markets are seeking consistently large fruit and paying premium prices for it.

TABLE 4

Fruit size characteristics of blueberry cultivars, Rowan, NC. 2005-2007 averages.

| | Wt./berry[1] | Cumul. % with diameters greater than | | |
|---|---|---|---|---|
| Cultivar | Grams | 18 mm | 16 mm | 12 mm |
| New Hanover | 1.43ab | 3 | 27 | 97 |
| O'Neal | 1.22b | 1 | 12 | 88 |
| Pinnacle | 1.73a | 20 | 54 | 97 |

[1]Numbers not followed by the same letter are significantly different (LSD 0.05).

Fruit Color:

In addition to The Royal Horticultural Society Colour Chart, fruit color was also determined objectively by a Minolta Color Meter (Table 5). The Minolta Color Meter demonstrated that 'Pinnacle' was equal to or better than 'New Hanover' for fruit color in 2005 and 2006. It was superior to 'O'Neal' both years. Averaged across the two years there were no significant differences (n.s.) among the three cultivars. However the actual "L" value for 'Pinnacle' was higher than the other two.

TABLE 5

Fruit color of blueberry cultivars at Castle Hayne, NC. 2005 and 2006.

| Cultivar | Average L value[1,2] 2005 | 2006 | Average |
|---|---|---|---|
| New Hanover | 20.5a | 20.7b | 20.6 n.s. |
| O'Neal | 18.8b | 20.2b | 19.5 n.s. |
| Pinnacle | 20.7a | 23.7a | 22.2 n.s. |

[1]Color (lightness or "L" values) determined objectively by a Minolta Color Meter, Model CR-110, Minolta, Ramsey, NJ. Higher values indicate lighter blue color. Meter not operational in 2007.
[2]Numbers not followed by the same letter are significantly different (LSD 0.05);
n.s. = not significant.

Fruit Firmness:

Fruit firmness was determined by a Firm Tek Firmness Tester (Table 6). 'Pinnacle' was equal or superior to 'New Hanover' for firmness all three years and for the overall average. It was superior to 'O'Neal' in 2005, 2006 and for the overall average. Fruit firmness is definitely another of the strong points of 'Pinnacle'.

TABLE 6

Fruit firmness of blueberry cultivars at Castle Hayne, NC. 2005-2007.

| Cultivar | Fruit firmness (grams/mm)[1,2] 2005 | 2006 | 2007 | Average |
|---|---|---|---|---|
| New Hanover | 178.6a | 173.9b | 196.0 n.s. | 182.7a |
| O'Neal | 148.2b | 165.5b | 183.2 n.s. | 165.5b |
| Pinnacle | 173.9a | 205.3a | 186.8 n.s. | 188.9a |

[1]Determined by a Firm Tek II firmness tester (Firm Tek, Salina, KS). Higher numbers indicate firmer fruit.
[2]Numbers not followed by the same letter are significantly different (LSD 0.05);
n.s. = not significant.
[3]Only three reps available.

Fruit Flavor:

Subjective ratings for fruit flavor determined that 'Pinnacle' was superior to 'New Hanover' all three individual years, and equal to 'New Hanover' for the overall average (Table 7). It was superior to 'O'Neal' all three years and for the overall average. Ratings for 'Pinnacle' were consistently in the very good range (high 70s) and showed less variability than 'New Hanover' or 'O'Neal'.

TABLE 7

Flavor ratings for blueberry cultivars at Rowan, NC. 2005-2007.

| Cultivar | Flavor ratings)[1,2] 2005 | 2006 | 2007 | Average |
|---|---|---|---|---|
| New Hanover | 76.8b | 74.5b | 77.2b | 76.2ab |
| O'Neal | 76.0b | 72.1c | 75.4c | 74.5c |
| Pinnacle | 78.3a | 76.9a | 78.1a | 77.7a |

[1]Subjective rating scale where less than 60 is unsatisfactory, 60-69 is acceptable, 70-75 is good, 76-79 is very good, and 80 and above superior.
[2]Numbers not followed by the same letter are significantly different (LSD 0.05).

Post Harvest Shelf-Life:

Post harvest studies to determine the percent marketable fruit after seven days with fruit held at 40° F. or 70° F. demonstrated that there were no significant differences among the cultivars and that all had very good post-harvest shelf-life characteristics (Table 8).

TABLE 8

Post-harvest shelf-life of the fruit of blueberry cultivars, Castle Hayne, NC. 2007-2009

| Cultivar | Percent sound fruit after 7 days at 40° F.[1] | 70° F.[2] |
|---|---|---|
| New Hanover | 90.3 n.s. | 53.2 n.s. |
| O'Neal | 87.0 n.s. | 67.8 n.s. |
| Pinnacle | 84.6 n.s. | 60.9 n.s. |

[1]Average for 2007-2009.
[2]Average for 2008 and 2009.
n.s. = not significant

Propagation:

'Pinnacle' is easily propagated asexually by both hardwood and softwood stem cuttings. All plants have remained true to type across all generations of asexual propagation.

Chilling Requirement:

Dormant buds on plants of 'Pinnacle' require 600-700 hours of temperatures below 45° F. to break dormancy in spring.

Soil Adaptation:

The original seedling plant of 'Pinnacle' was growing in pot culture at Beltsville, Md., in a "Berryland" soil. In North Carolina plants of 'Pinnacle' have performed well following establishment in Berryland soil or a very similar soil type. Therefore, it is recommended that 'Pinnacle' be established on sites with Berryland or very similar soil types.

Disease Reaction:

'Pinnacle' has not been observed to have problems with either of the major fungal diseases affecting blueberries in North Carolina, stem canker (*Botryosphaeria corticis*) and stem blight (*Botryosphaeria dothidea*) up to this time.

Herbarium Voucher:

A voucher of 'Pinnacle' will be deposited in the Herbarium of North Carolina State University (NCSU) in Raleigh, N.C., USA, upon patenting.

DNA Fingerprinting

During the past three decades several biochemical and DNA based assays have been developed to fingerprint human and plants. While biochemical assays such as isozymes were among the very first ones that were developed but they are limited in number and time consuming to generate. Genetic information is stored in cells as DNA, a long molecular chain, on which the linear order of four chemicals (called A, C, G, and T nucleotides) constitute individual genes. DNA based markers including restriction fragment length polymorphism (RFLP)[1], random amplified polymorphic DNA (RAPD)[2], amplified fragment length polymorphism (AFLP)[3], simple sequence repeats (SSRs)[4], single nucleotide polymorphism (SNP)[5], single position polymorphism (SPP)[6], and targeted region amplification polymorphism (TRAP)[7]. Genotyping with molecular markers is used for cultivar fingerprinting, detection of genetic diversity, assessment of population structure, mapping genes of interest, and for selection of desirable genotypes in breeding programs. The coding sequences of DNA that make up the genes are interrupted by long stretches of DNA that do not code for proteins and which are consequently called "non-coding DNA" or more loosely referred to as "junk DNA". In this "junk DNA", there are numerous chromosomal locations that contain short stretches of DNA where a particular sequence of 2-8 nucleotides is repeated in tandem a number of times.

Figure 4:
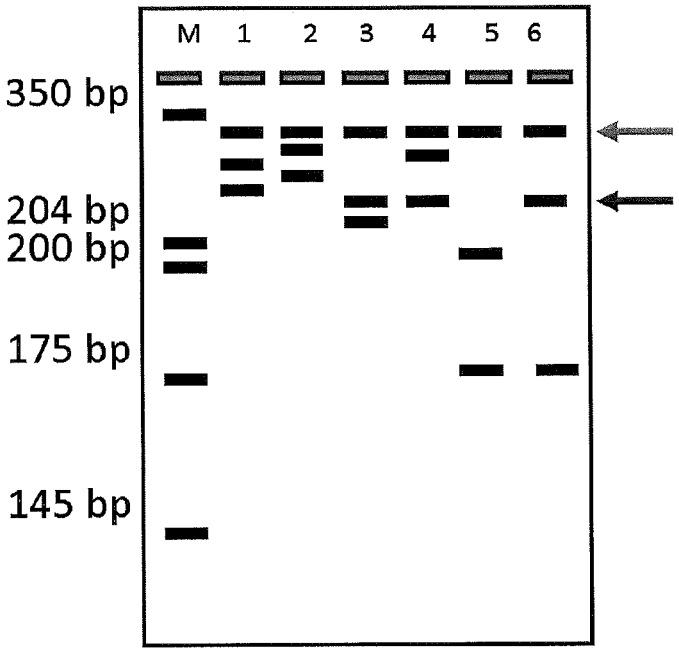
FIG. 4 shows a hypothetical example of one SSR marker on a panel of 6 cultivars depicted as 1-6. The lane marked as M shows the standard marker lane with known fragment size in base pair (bp). The top arrow shows a monomorphic band that is identical in all cultivars. The bottom arrow shows a band that is monomorphic in cultivar 3, 4 and 6. Therefore the other band can be used to distinguish these three cultivars from each other. This profile for these cultivars is based on one markers. As the number of markers increase the probability that two literally different cultivars have the same profile will reduced.
Figure 5:
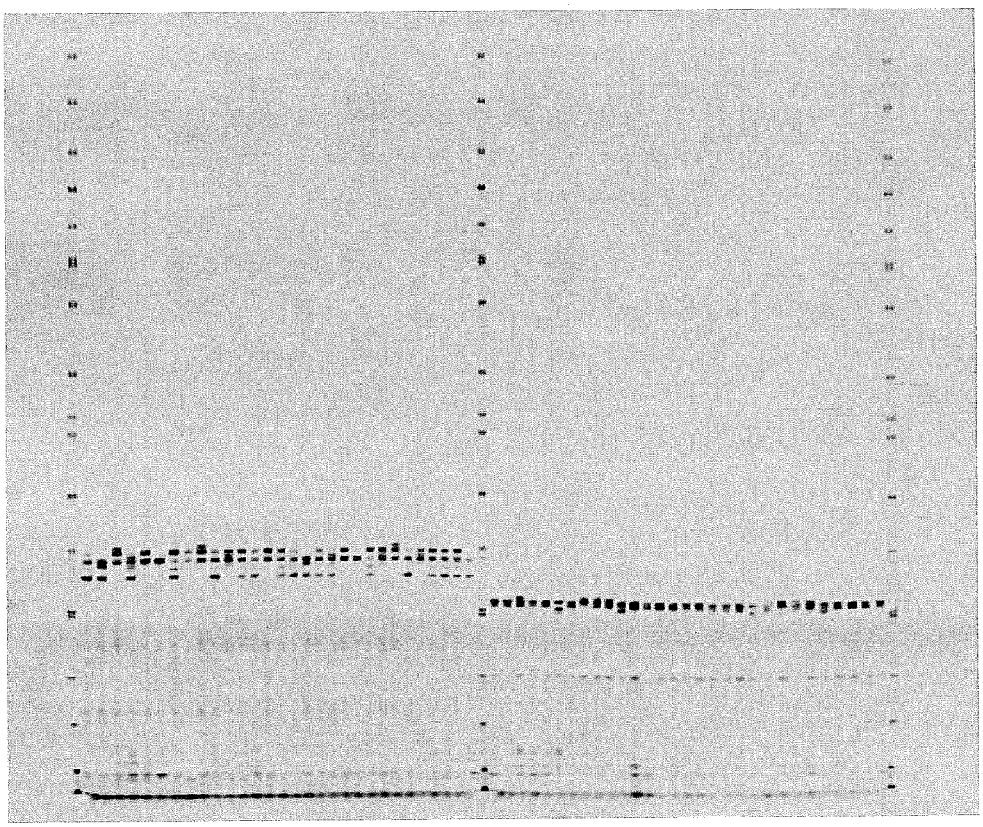
FIG. 5 provides a gel electrophoresis picture of two SSR markers run on 30 blueberry cultivars. The profile of the two SSR markers for different cultivars are different and shows that while the marker on the left hand side shows more polymorphism, the marker in the right hand side is less informative for distinguishing the cultivars.

These repeat units, known as SSRs, or microsatellites, occur at the same chromosomal location, called "locus" and, although they are inherited stably from parent to child, they vary substantially between individuals. SSR markers are tandem repeats of di-, tri-, tetra- or penta-nucleotides. For instance, common motif is ACn, where the two nucleotides A and C are repeated tandemly n times. The polymorphism occurs between two or more different cultivars when n differs among them. In another word, one cultivar can be $AC_{40}$ and another $AC_{50}$. The fragments can then be separated by size (bp=base pairs) on an electrophoresis gel and individuals can be genotyped for their allelic composition (homozygote or heterozygote for one or more alleles). Gel electrophoresis is a method for separation and analysis of macromolecules (DNA, RNA and proteins) and their fragments, based on their size and electrical charge (FIGS. 4 and 5). When these fragments amplified by polymerase chain reaction (PCR), one cultivar generates an 80 bp and other generates a 100 bp fragment, respectively. Usually amplification occurs in multiple locations in the genome (alleles), resulting multiple fragments with different sizes. A number of fragments will not be polymorphic between any two cultivars. Usually a few fragments will have different sizes that can be used to differential cultivars. Since each fingerprint is unique, therefore the profile of each cultivar must be checked against a pool of other cultivars that have been tested before.

Figure 6:
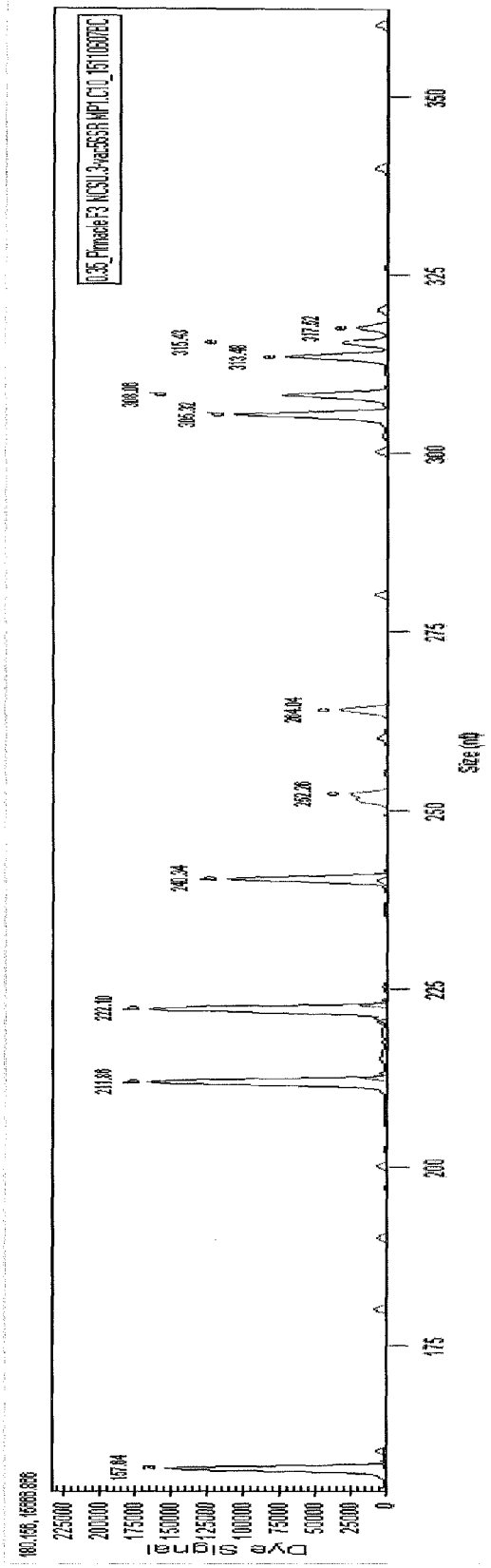
FIG. 6 shows an electropheorgram of 5 SSR markers that were run on a blueberry cultivar (Pinnacle), depicting the fragment sizes of each marker in different color. Marker 1 generated a 157 fragment, Marker 2, fragments 212, 221, and 240, Marker 3, fragments 251, 263, Marker 4, fragments 304 and 307, Marker 5, fragments 313, 315 and 317.
Figure 7:
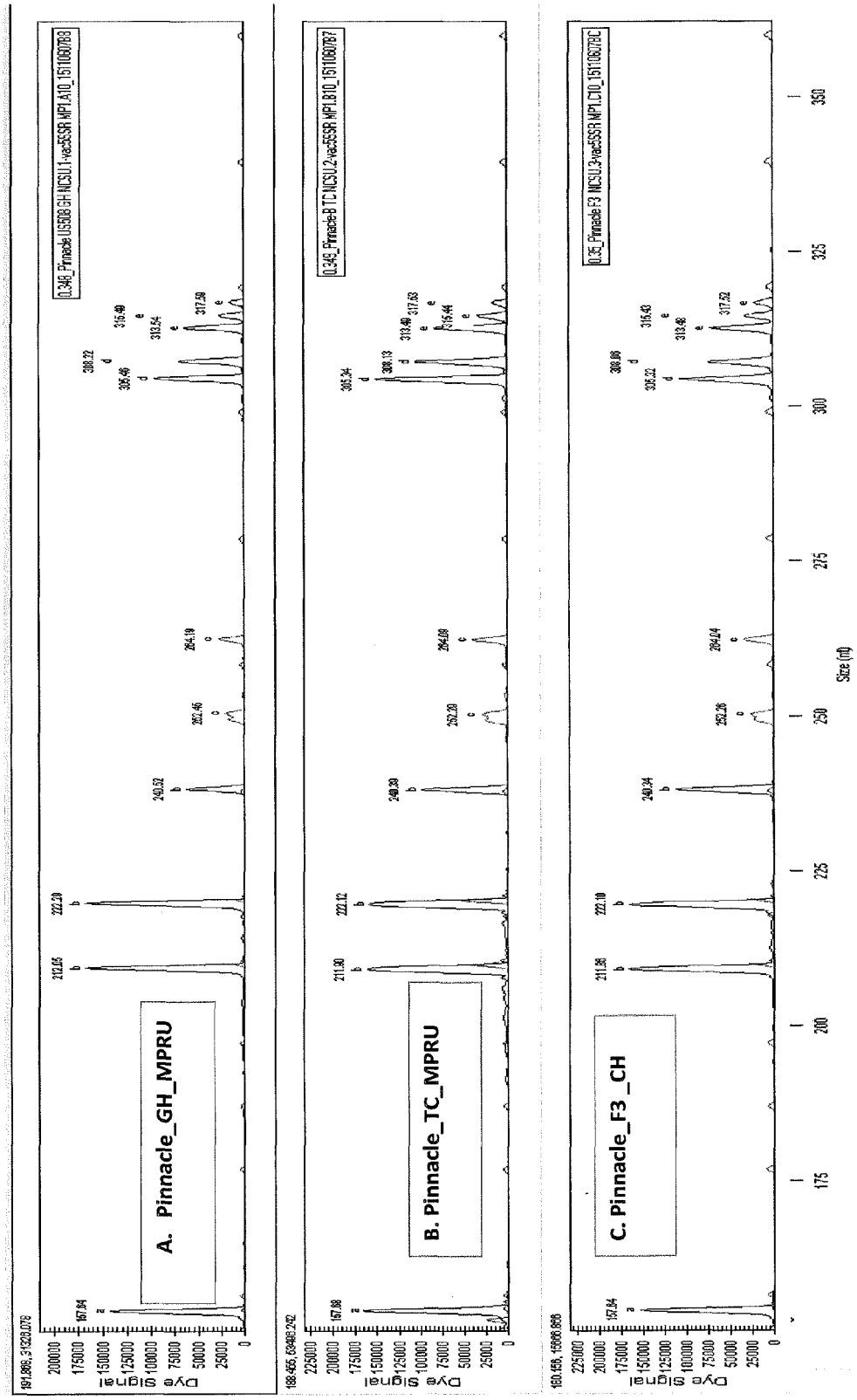
FIG. 7 shows the fingerprint profile of the Pinnacle based on five SSR markers. Each peak is corresponding to one allele of markers that were being used. Panel (A) is a Pinnacle sample collected from greenhouse of the Micropropagation and Repository Unit (MPRU), (B) is the same cultivar grown on tissue cultured media and (C) cultivar Pinnacle collected from field F3 of Horticultural Crop Research Station in Castle Hayne, N.C.

By the advent of capillary electrophoresis machines in late 1990s-early 2000s, the use of gel electrophoresis to run SSR markers has been declined. First, because casting and loading the gels are cumbersome. Second, running and scoring the gels are time consuming and sometimes there is no clear distinction between very close bands which makes the scoring inaccurate. The output of capillary machines is an electropherogram similar to the one is shown in FIG. 6.

A population database for blueberry has been developed at National Clonal Germplasm Repository in Corvallis (Oreg.), the most diverse global live genbank for blueberry and wild relatives, which includes over 1700 accessions from 39 countries and 81 blueberry species. They have genotyped these cultivars and accessions and created database of profiles for all genotypes that have been fingerprinted.

DNA Profiling of Pinnacle

Plant Materials: Leaf tissues of Pinnacle cultivar were collected from the field at the Horticultural Crops Research Station in Castle Hayne, N.C. as well as samples at Micropropagation and Repository Unit (MPRU) in Raleigh, N.C. This allowed us to compare the samples in the field with those that were used in tissue culture facility (MPRU) to make sure they are identical and the true types. The leaf tissues were kept in −80 freezer until they were used for DNA extraction.

DNA extraction: The DNA from frozen leaf tissue was extracted using QIAGEN DNeasy plant Mimi Kit (cat # 69104), according to manufacturer's recommendation. DNA quantity was measured using Qbit 3.0 Fluorometer (Invitrogen, Carlsbad, Calif., USA) and Nanodrop [8] instruments.

PCR amplification: The polymerase chain reaction (PCR) was carried out on a Bio-Rad DNA Engine Dyad PTC0220 thermocycler. A multiplexed PCR primer master mix containing 2 μM of each primer was used to assay 5 markers in the same reaction (Table 1). The QIAGEN, Type-It® kit containing Taq DNA polymerase and other PCR components was used for amplification of DNA followed by manufacturer's recommendations.

The thermocycler programmed according to QIAGEN recommendation. Briefly, an initial DNA denaturation and hot start step at 98° C. for 5 minutes, followed by 29 cycles of 95° C. for 30 sec, 57° C. for 1.5 min and 72° C. for 30 sec. A final extension was applied at the end of 29 cycles at 60° C. for 30 min and the samples were kept at 4° C. until further analyses were carried out.

TABLE 9

List of SSR markers, their names, size range, repeat motif, linkage group (LG) on a genetic linkage map, forward and reverse primers.

| SSR name | Size range | Motif | LG | Forward (5'-3') sequence |
|---|---|---|---|---|
| CA23 | 154-175 | (AGA)6 | 10 | GAGAGGGTTTCGAGGAGGAG |
| Contig179F | 195-240 | (AGT)5 | 9 | CGTCGTGGAGGCTTAGAAAG |
| CfC262 | 237-287 | (CAC)8 | 2 | CGCCCACTCAGTTCATTCTT |
| NA172F | 295-313 | (CAT)5 | 4 | CCTCGTCCTCCTCTTCCTCT |
| Vac.288135 | 291-333 | (GAG)15 | 10 | TCTCTTTCCUTTTCAAGTGG |

| SSR name | Reverse (5'-3') sequence |
|---|---|
| CA23 | GTTTAGAAACGGGACTGTGAGACG |
| Contig179F | GTTTCAAAATCACCAGCACCAA |
| CfC262 | ATAGGTGGTGGCTGGTGAGT |
| NA172F | GITTGACTUGGAGAAGGCGAAG |
| Vac.288135 | GTTTATGATGGAATTCCGAGTTTG |

Detection: The size of each SSR marker was determined by Beckman Coulter CEQ 8000 Genetic Analysis System. This system automatically fills the capillary array with a patented linear polyacrylamide (LPA) gel, denatures and loads the sample, applies the voltage program, and analyzes the data, Results: Pinnacle generated a unique profile, which did not match with all cultivars that have been genotypes at National Clonal Germplasm Repository in Corvallis (Oreg.) (Table 2). The sample that was collected from our experimental station in Castle Hayne and the samples collected from MPRU (Tissue cultured plants in greenhouse and the plants that were still in the growth chamber in tissue culture media), all three generated identical profile indicating that they are true types in both locations. We cannot calculate the probability of finding an exact match with Pinnacle in all blueberry populations, because allele frequency of all SSR alleles at all loci has not been calculated for blueberry. However, probability of all 11 alleles of the 5 markers tested is closed to zero.

TABLE 10

The fingerprint profile of the Pinnacle based on five SSR markers.
The numbers after the "-" designate the allele (different form) number of each marker.

| Sample | CA2 3-1 | Contig17 9-1 | Contig17 9-2 | Contig17 9-3 | CFC26 2-1 | CFC26 2-2 | NA17 2-1 | NA17 2-2 | Vac.28813 5-1 | Vac.28813 5-2 | Vac.28813 5-3 |
|---|---|---|---|---|---|---|---|---|---|---|---|
| Pinnacle_GH_MP RU | 157 | 212 | 221 | 240 | 251 | 263 | 304 | 307 | 313 | 315 | 317 |
| Pinnacle_TC_MP RU | 157 | 212 | 221 | 240 | 251 | 263 | 304 | 307 | 313 | 315 | 317 |
| Pinnacle_F3_CH | 157 | 212 | 221 | 240 | 251 | 263 | 304 | 307 | 313 | 315 | 317 |

1. Saiki R K, Scharf S, Faloona F, Mullis K B, Horn G T, Erlich H A, Arnheim N: Enzymatic amplification of beta-globin genomic sequences and restriction site analysis for diagnosis of sickle cell anemia. *Science* 1985, 230(4732): 1350-1354.
2. Williams J G, Kubelik A R, Livak K J, Rafalski J A, Tingey S V: DNA polymorphisms amplified by arbitrary primers are useful as genetic markers. *Nucleic Acids Res* 1990, 18(22):6531-6535.
3. Vos P, Hogers R, Bleeker M, Reijans M, Lee Tvd, Homes M, Friters A, Pot J, Paleman J, Kuiper M et al: AFLP: a new technique for DNA fingerprinting. *Nucleic Acids Res* 1995, 23(21):4407-4414.
4. Tautz D: Hypervariability of simple sequences as a general source for polymorphic DNA markers. *Nucleic Acids Res* 1989, 17(16):6463-6471.
5. Collins F S, Guyer M S, Charkravarti A: Variations on a theme: cataloging human DNA sequence variation. *Science* 1997, 278(5343):1580-1581.
6. Stoffel K, van Leeuwen H, Kozik A, Caldwell D, Ashrafi H, Cui X, Tan X, Hill T, Reyes-Chin-Wo S, Truco M-J et al: Development and application of a 6.5 million feature affymetrix genechip® for massively parallel discovery of single position polymorphisms in lettuce (*Lactuca* spp.). *BMC Genomics* 2012, 13(1):185.
7. Palumbo R, Hong W-F, Wang G-L, Hu J, Craig R, Locke J, Krause C, Tay D: Target Region Amplification Polymorphism (TRAP) as a Tool for Detecting Genetic Variation in the Genus Pelargonium. *HortScience* 2007, 42(5):1118-1123.
8. Desjardins P, Conklin D: NanoDrop Microvolume Quantitation of Nucleic Acids. *Journal of Visualized Experiments : JoVE* 2010(45):2565.

What is claimed is:

1. A new and distinct variety of commercial blueberry plant (*Vaccinium corymbosum* Linnaeus) named 'Pinnacle' substantially as illustrated and described herein, characterized by its early season ripening, good yields of large size fruit, including a high percentage of fruit in very large diameter categories, very good fruit color and quality, and excellent fruit firmness, along with good post-harvest shelf-life of the fruit.

* * * * *